(12) United States Patent
Beyer

(10) Patent No.: US 8,979,810 B1
(45) Date of Patent: Mar. 17, 2015

(54) NASAL ASPIRATION SYSTEMS AND RELATED METHODS

(76) Inventor: Craig Beyer, Boulder, CO (US)

( * ) Notice: Subject to any disclaimer, the term of this patent is extended or adjusted under 35 U.S.C. 154(b) by 868 days.

(21) Appl. No.: 12/392,927

(22) Filed: Feb. 25, 2009

Related U.S. Application Data

(60) Provisional application No. 61/031,208, filed on Feb. 25, 2008.

(51) Int. Cl.
- *A61M 1/00* (2006.01)
- *A61M 31/00* (2006.01)
- *A61F 5/44* (2006.01)
- *A61M 5/00* (2006.01)

(52) U.S. Cl.
USPC ........ 604/317; 604/319; 604/327; 604/94.01; 604/335; 604/345; 604/173

(58) Field of Classification Search
USPC ........ 604/94.01, 289, 126, 118–119, 173, 35, 604/317, 319, 327, 335, 345
See application file for complete search history.

(56) References Cited

U.S. PATENT DOCUMENTS

| | | | |
|---|---|---|---|
| 4,403,611 A * | 9/1983 | Babbitt et al. | 604/73 |
| 4,422,456 A * | 12/1983 | Tiep | 128/207.18 |
| 4,681,571 A * | 7/1987 | Nehring | 604/320 |
| 5,183,467 A * | 2/1993 | Mouney | 604/149 |
| 5,246,666 A | 9/1993 | Vogler et al. | |
| 5,257,633 A | 11/1993 | Vogler et al. | |
| 5,320,812 A | 6/1994 | Harper | |
| 5,326,535 A | 7/1994 | Vogler et al. | |
| 5,344,611 A | 9/1994 | Vogler et al. | |
| 5,533,506 A * | 7/1996 | Wood | 128/207.18 |
| 6,238,377 B1 * | 5/2001 | Liu | 604/289 |
| 6,736,792 B1 * | 5/2004 | Liu | 604/94.01 |

OTHER PUBLICATIONS

Vacutainer, accessed on the Internet Sep. 26, 2011, http://en.wikipedia.org/wiki/Vacutainer, 4 pages.

* cited by examiner

*Primary Examiner* — Bhisma Mehta
*Assistant Examiner* — Bradley G Thomas, Jr.
(74) *Attorney, Agent, or Firm* — Lathrop & Gage LLP

(57) ABSTRACT

A nasal aspiration system for removing secretions from the user's nasal canals includes a port having a cap and a vacuum canister coupled on opposite ends. The cap includes two aspiration tubes extended therefrom. The aspiration tubes are configured for inserting into a user's nasal canals. The port includes a valve disposed therein, where the valve is operable to control the flow of nasal secretion from the aspiration tubes into the vacuum canister.

8 Claims, 4 Drawing Sheets

US 8,979,810 B1

NASAL ASPIRATION SYSTEMS AND RELATED METHODS

RELATED APPLICATIONS

This application claims benefit of priority to U.S. Provisional Application Ser. No. 61/031,208 filed Feb. 25, 2008, which is incorporated herein by reference.

BACKGROUND

During athletic activities such as skiing or swimming, it is challenging to have to carry facial tissue. For example, during skiing, it is difficult to remove gloves in the cold to pull facial tissues out of a pocket. Further, there are typically no trash-cans available on a ski slope to dispose of the used facial tissues, thereby leading people to leave used facial tissues on the ground, which equates to pollution. Additionally, used facial tissues are loaded with potential infectious nasal secretions that typically harbor contagious bacteria and viruses. When a person blows his/her nose into a facial tissue or handkerchief and then throws it away or folds it up to put back into a pocket, infectious agents are spread and transmitted to others. Likewise, facial tissues cannot be carried during swimming—most people simply blow their noses into the swimming pool water, creating an unsanitary environment.

Furthermore, blowing nasal secretions from the nose creates a positive pressure in the Eustachian tubes that connect the nasal passages to the middle ears. This positive pressure can also force nasal secretions into the middle ears, creating a middle ear infection. Highly fragile tympanic membranes lie directly adjacent to the middle ears and can be easily damaged by middle ear positive pressure.

SUMMARY

In one embodiment, a nasal aspiration system for removing secretions from the user's nasal canals includes a port coupled between a cap and a vacuum canister. The cap includes two aspiration tubes extended therefrom. The aspiration tubes are configured for inserting into a user's nasal canals. The port includes a valve disposed therein, wherein the valve is operable to control flow of nasal secretion from the aspiration tubes into the vacuum canister.

In one embodiment, a nasal aspiration system for removing secretions from nasal canals includes a canister, a cap, and a port which is coupled between the vacuum canister and the cap. The cap has two aspiration tubes extended therefrom, for inserting into a user's nasal canals. The port includes a conduit and a vacuum source disposed therein, where the vacuum source is operable to control the flow of nasal secretion from the aspiration tubes into the vacuum canister. In one embodiment, a method for operating a nasal aspiration system to aspire nasal secretion from a user's nasal canals includes the steps of aligning the aspiration tubes to a proper distance between the nasal canals, inserting the aspiration tubes with disposable nasal occluders directly into the nasal canals of a user, activating an aspiration force of a nasal aspiration system, aspirating secretions from the user's nasal canals, and withdrawing the aspiration tubes with the disposable nasal occluders from nasal canals.

DETAILED DESCRIPTION

Nasal aspiration systems and methods are described in relation to removal of nasal secretions; however, these systems and methods may be used for aspiration of other bodily secretions/excretions. For example, a similar aspiration system may be used to help empty a bladder of people with poor bladder emptying capabilities, such as people with hypotonic bladders.

In the attached drawings, for the sake of clarity of illustration, multiple elements within figures may not be labeled and the figures may not be drawn to scale.

Figure 1:
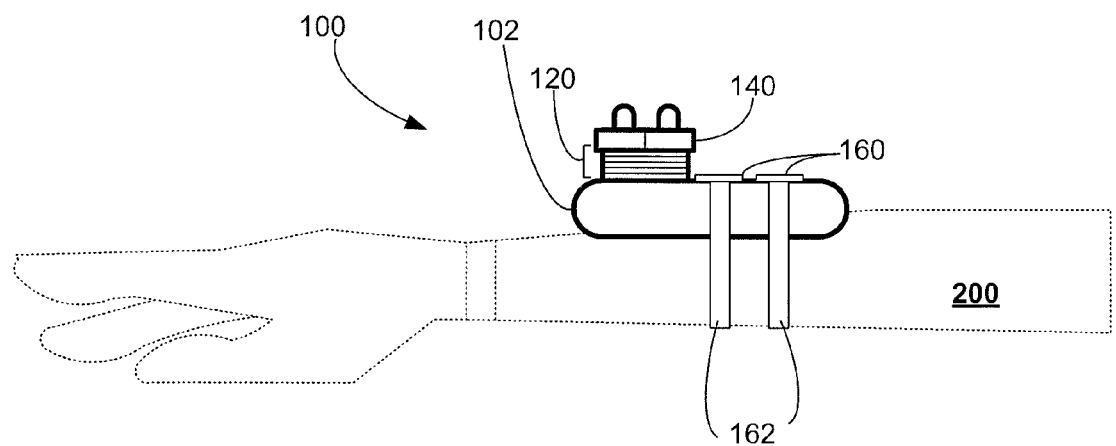
FIG. 1 shows a side view of the nasal aspiration system fastened to a user's arm.

FIG. 1 shows a side view of nasal aspiration system 100 fastened to a user's arm 200. Nasal aspiration system 100 includes cap 140, a port 120, and a vacuum canister 102. As described further below, cap 140 is removably connected to a first end of port 120 and the vacuum canister 102 is removably attached to a second end of port 120. Cap 140 includes aspiration tubes (e.g., aspiration tubes 144, 145 of FIG. 2) for inserting into a user's nasal canals. Port 120 includes a valve (e.g., valve 122 of FIG. 3) for controlling the flow of the nasal secretion between cap 140 and vacuum canister 102. Vacuum canister 102 contains negative pressure to provide a vacuum force for nasal aspiration system 100. Vacuum canister 102 may be detachable; for example, when the vacuum force within it is depleted or when it is filled with nasal secretions, vacuum canister 102 may be disposed and replaced with a new vacuum canister.

One or more straps 162, releasably linked with one or more restraints 160, may be used to fasten system 100 to a user's arm 200. In an alternative embodiment, straps 162 may be replaced with a variety of fastening systems that permit system 100 to be secured to various parts of the body without departing from the scope hereof.

Figure 2:
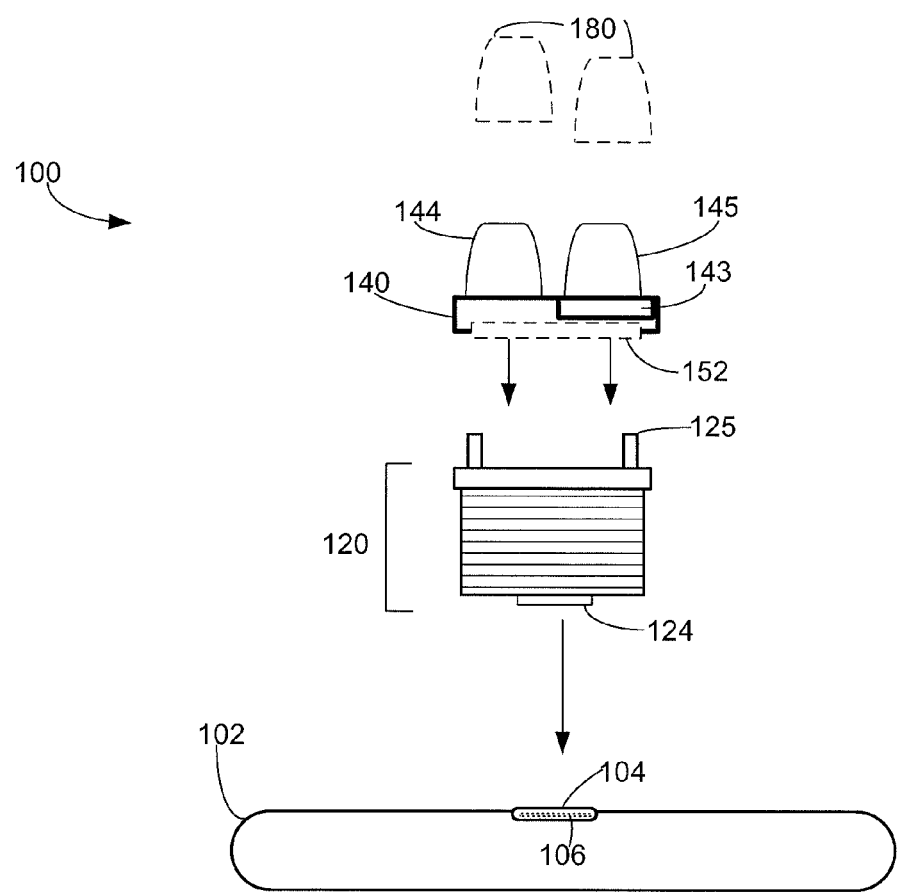
FIG. 2 shows the nasal aspiration system of FIG. 1 in further detail, in accord with an embodiment.

FIG. 2 shows nasal aspiration system 100 of FIG. 1 in further detail. As described above, system 100 includes port 120; a cap 140 and vacuum canister 102 couple to opposite ends of port 120. Cap 140 includes aspiration tubes 144, 145 extended therefrom. At least one aspiration tube is adjustable (to set distance between tubes 144, 145) for selectively aligning aspiration tubes 144, 145 with the user's nasal canals (not shown). In an alternative embodiment, cap 140 may be removable to accommodate different nostril sizes. Nasal occluders 180 may optionally be used to cover aspiration tubes 144, 145 during use and disposal of cap 140.

Vacuum canister 102 includes an attachment device 104 configured to attach to the second end of port 120. A protective film 106 is disposed with attachment device 104 to retain vacuum (e.g., negative pressure) within vacuum canister 102. Protective film 106 may be plastic, foil, or the like.

FIG. 2 shows port 120 includes attachment mechanisms 125 and 124, disposed at first and second ends of cap 140, configured to couple with corresponding attachment mechanism 152, 104 of cap 140 and vacuum canister 102, respectively. Attachment mechanisms 104, 124, 125, 152 may be one or more notches, snaps, clasps, protrusions, pipes, indentations, apertures, recesses, taps, clips, adhesives, or other fasteners or combination thereof. In one example, attachment mechanisms 104, 152 represent threaded apertures and attachment mechanisms 124, 125 represent threaded pipes to enable the coupling of vacuum canister 102 and cap 140, respectively, to port 120. In an alternative embodiment, attachment mechanisms 124, 125 are press fitted onto the corresponding attachment mechanisms 104 and 152. Other attachment mechanisms may be used without departing from the scope hereof.

Figure 3:
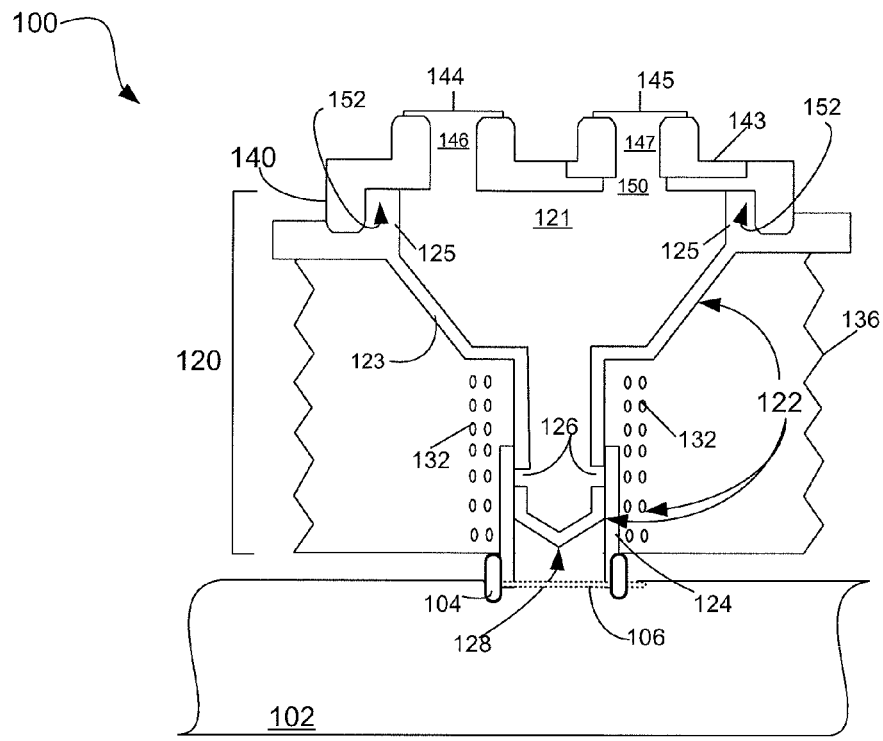
FIGS. 3-4 show a vertical cross-section through the nasal aspiration system of FIGS. 1 and 2, illustrating internal detail, in accord with an embodiment.

FIG. 3 shows a vertical cross-section view through system 100 in a non-operational position, illustrating internal detail. FIG. 3 shows a cross-section view of cap 140, port 120, and vacuum canister 102 of system 100. Cap 140 is configured to removably attach to port 120 having one aspiration tube 144 extended therefrom. Inlet 146 is formed within aspiration tube 144 to receive secretions from a user's nasal canals. An aperture 150 is formed on cap 140 adjacent to aspiration tube 144. An adjustable slider 143, having an aspiration tube 145 extended therefrom, is coupled to the top of cap 140 to partially cover aperture 150. Once coupled, the distance between aspiration tube 144 and 145 can be adjusted by moving adjustable slider 143 in a coplanar direction with cap 140. In such an embodiment, aspiration tube 144 remains fixed as aspiration tube 145 is moved to accommodate varying distances of different user nasal canals. Inlet 147, formed within aspiration tube 145, aligns on top of aperture 150 to receive secretions from the second nostril of the user's nasal canals. Aperture 150 is sufficiently large enough to accommodate the varying location of inlet 147 as aspiration tube 145 is slid closer or further away from aspiration tube 144. In an alternative embodiment, aspiration tubes 144, 145 may both be adjustable. In this embodiment, two adjustable sliders (e.g., similar to adjustable slider 143) are disposed on top of cap 140 such that tubes 144, 145 may both be slid closer or further away from each other. Each of the two adjustable sliders has an aspiration tube extended therefrom. Two apertures 150 form on top of cap 140 and are configured to align and receive the two inlets from the two adjustable tubes. Attachment mechanism 152 forms on the bottom of cap 140 and is configured to receive attachment mechanism 125 of port 120, thereby coupling cap 140 with port 120.

Port 120 includes a valve 122. Valve 122 includes a conduit 123 having a pointed end 128, spring 132, and attachment mechanism 124. A cavity 121 is formed on conduit 123 opposite of pointed end 128. As shown, the diameter of cavity 121 is large enough to provide clearance to accommodate the adjustment of inlets 146, 147 of aspiration tubes 144, 145. Outlets 126 are formed on the sides of conduit 123. Outlets 126 and pointed end 128 are configured to fit securely within the first end of attachment mechanism 124 to form an airtight seal therewith, thus blocking outlets 126, as shown. The second end of attachment mechanism 124 is configured to attach to the corresponding attachment mechanism 104 of vacuum canister 102. Spring 132, attached to conduit 123, provides biased spring power to close valve 122, thereby maintaining system 100 in a non-operational position.

Sides 136 of port 120 may be flexible to accommodate movement of spring 132 such that conduit 123 slides vertically within attachment mechanism 124, thereby naturally biasing valve 122 to the non-operational position, shown in FIG. 3. In an embodiment, sides 136 of port 120 may provide the bias power for valve 122 and spring 132 may be omitted.

Figure 4:
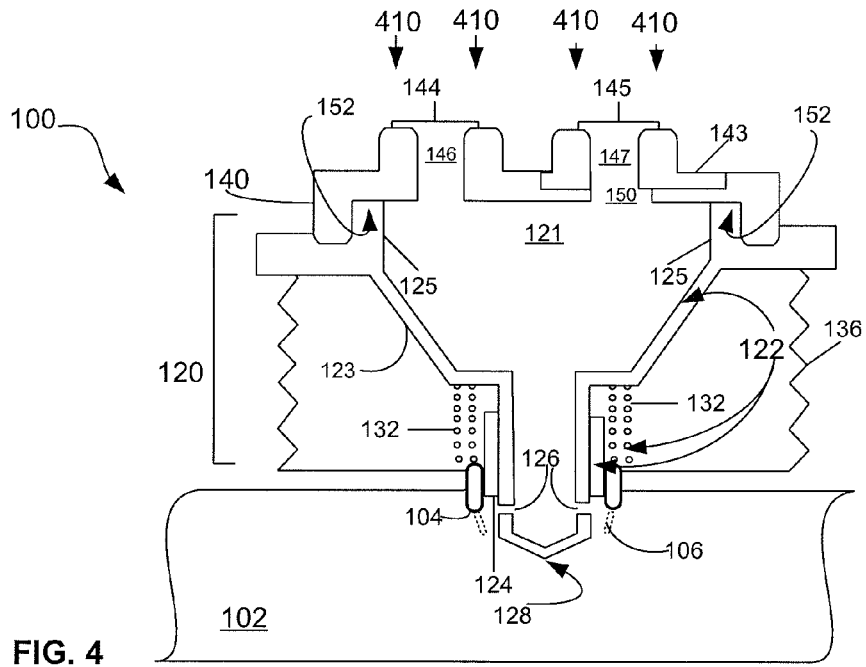

FIG. 4 shows a cross-sectional view of an assembled system 100 in an operational position, resulting from an external force 410 exerted upon the top (e.g., upon aspiration tubes 144, 145) of system 100 to overcome the bias power of spring 132 and/or sides 136. Upon a first operation of system 100, pointed end 128 penetrates protective film 106 (e.g., foil), thereby activating vacuum canister 102. Conduit 123 moves downward through attachment mechanism 124 such that outlets 126 are extended beyond the second end of attachment mechanism 124 to the operational position shown in FIG. 4. In this position, the vacuum within vacuum canister 102 forces airflow from aspiration tubes 144, 145 into canister 102, carrying nasal secretions with it. In other words, nasal secretions are sucked into vacuum canister 102 upon operation of system 100. Upon release of force 410 to the top of port 120, conduit 123 is retracted to the non-operational position by spring 132, thus restricting the flow of air or fluids into vacuum canister 102.

Figure 5:
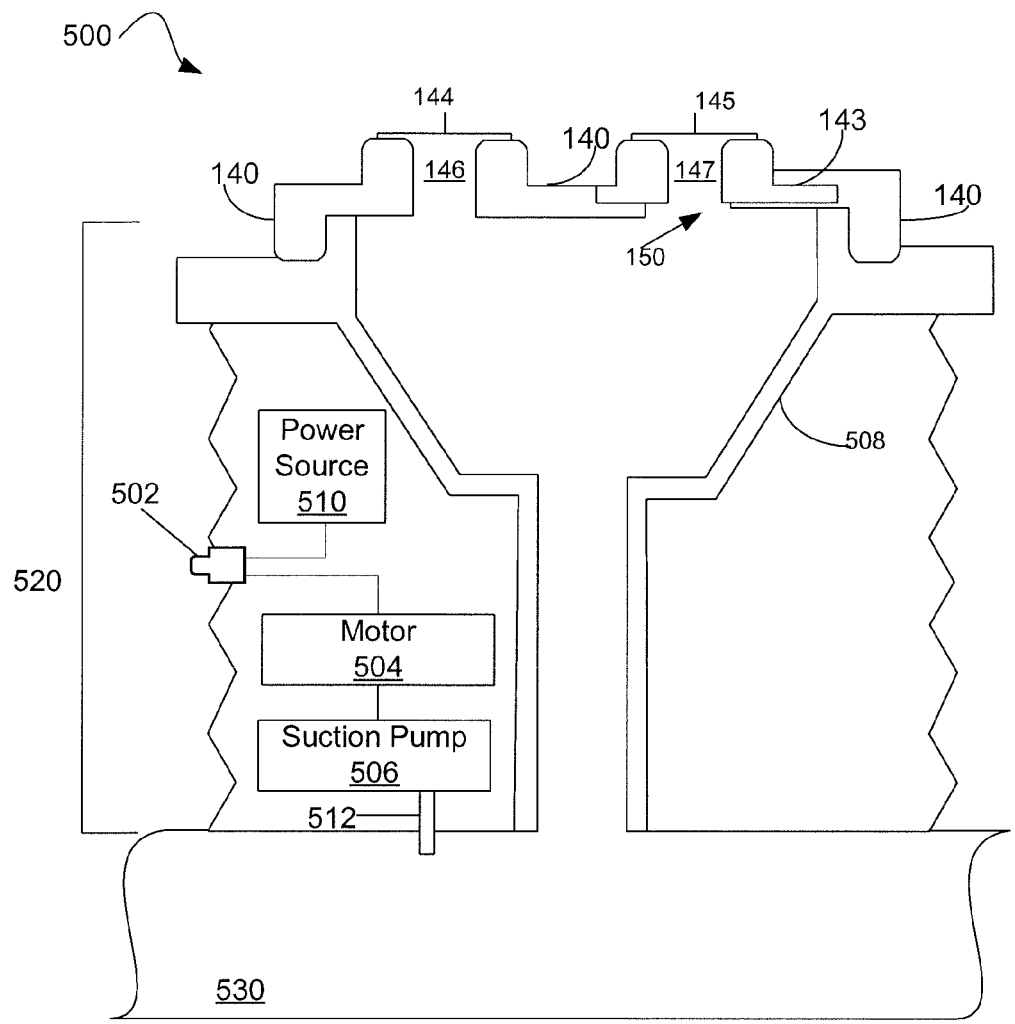
FIG. 5 shows a schematic view of a nasal aspiration system with a suction pump, according to an embodiment.

In an alternate embodiment, FIG. 5 shows a schematic view of a nasal aspiration system 500 that uses a suction pump 506 to create a vacuum within a canister 530. System 500 is similar to system 100, FIG. 1, but does not require that canister 530 contain a vacuum prior to operation. In particular, system 500 is shown having cap 120 with aspiration tubes 144, 145 extended therefrom. Cap 120 is configured to attach to a first end of tube 508 and a canister 530 is configured to attach to a second end of tube 530. Tube 530 disposes within a port 520. Port 520 includes a power source 510 connected to a motor 504 with a suction pump 506 via a switch 502. Suction pump 506 couples with canister 530 via a tube 512 such that upon operation of switch 502, power from power source 510 operates motor 504 to drive suction pump 506 that extracts air from canister 530 thereby creating a vacuum within canister 530.

In one example of operation, a user inserts aspiration tubes 144, 145 into the nostrils and operates switch 502. Motor 504 drives suction pump 506 to create a vacuum within 530 such that air and/or nasal secretions are sucked through aspiration tubes 144, 145, tube 508 and into vacuum canister 530.

Figure 6:
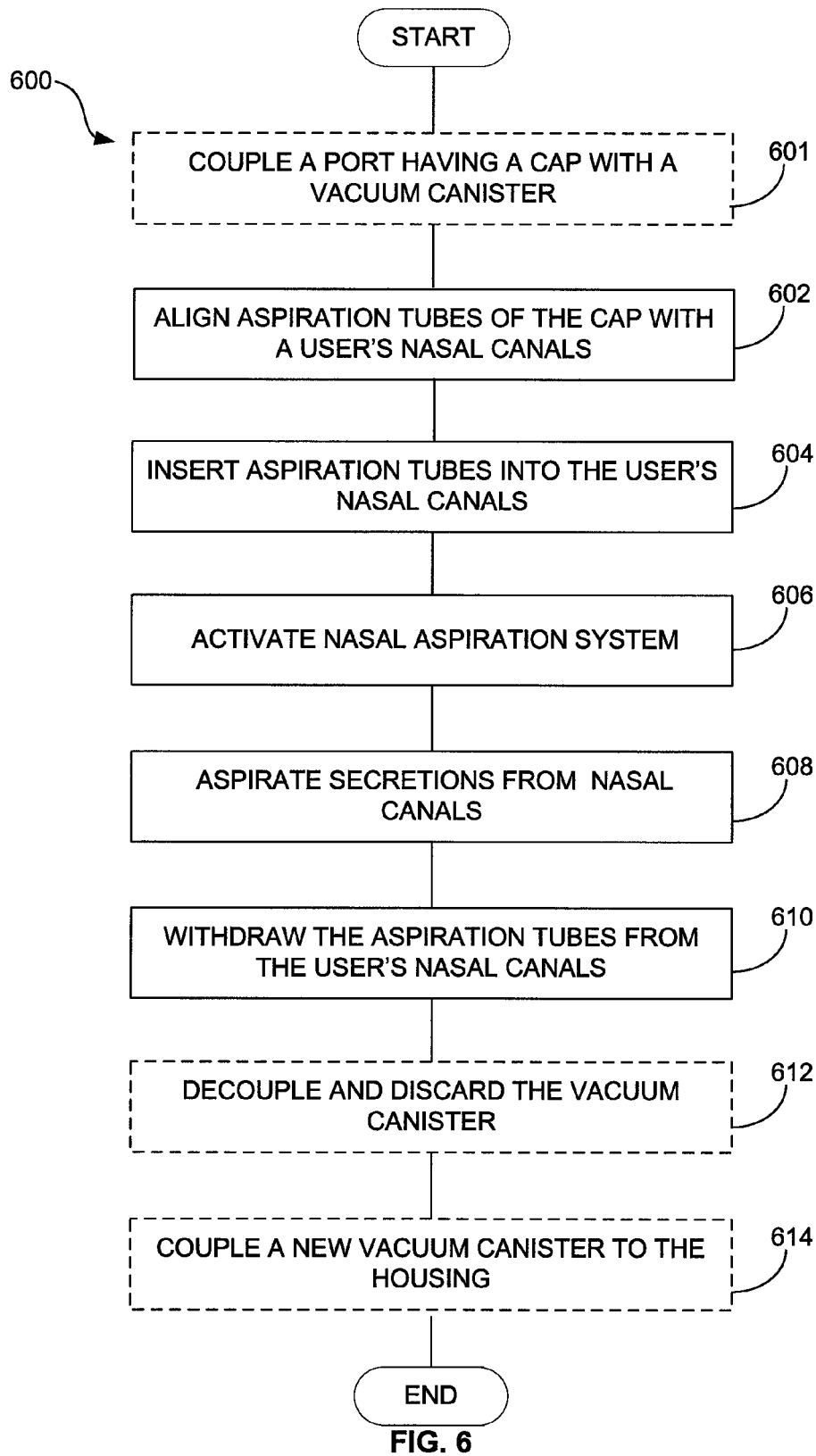
FIG. 6 is a flowchart illustrating one exemplary method for operating a nasal aspiration system, according to an embodiment.

FIG. 6 is a flowchart illustrating an exemplary method 600 for using nasal aspiration system 100 of FIG. 1. Step 601 is an optional step. In step 601, method 600 couples port 120 having a cap 140 with vacuum canister 102. In step 602, method 600 aligns aspiration tubes to the user's nasal canals. In one example of step 602, after covering the aspiration tubes 144, 145 with nasal occluders 180, the user adjusts aspiration tubes 144, 145 to align with his/her nostrils. In step 604, method 600 inserts aspiration tubes into the user's nasal canals. In one example of step 604, the user inserts aspiration tubes 144, 145 into his/her nostrils. In step 606, method 600 activates the nasal aspiration system. In one example of step 606, the user exerts force 410 to the top of aspiration tubes 144, 145 such that outlets 126 are unblocked by attachment mechanism 124. In step 608, method 600 aspirates secretions from the user's nasal canals. In one example of step 608, secretions from the user's nostrils are sucked through aspiration tubes 144, 145, conduit 123, and outlets 126 and are deposited into vacuum canister 102. In step 610, method 600 withdraws the aspiration tubes from the nasal canals. In one example of step 610, the user removes aspiration tubes 144, 145 (and nasal occluders 180, if used) from the nostrils, releasing force 410 and thereby stopping the suction. If used, nasal occluders 180 may be discarded or cleaned after each use. Step 612 is optional. In step 612, method 600 decouples and discards the vacuum canister. In one example of step 612, the user detaches port 120 from vacuum canister 102 and discards vacuum canister 102. In step 614, method 600 couples port 120 with a new vacuum canister 102.

It will be appreciated that the above-described steps may be performed in an order that differs from what is explicitly described without departing from the scope hereof.

The changes described above, and others, may be made in the systems and methods described herein without departing from the scope hereof. It should thus be noted that the matter contained in the above description or shown in the accompanying drawings should be interpreted as illustrative and not in a limiting sense. The following claims are intended to cover all generic and specific features described herein, as well as all statements of the scope of the present methods and systems, which, as a matter of language, might be said to fall there between.

What is claimed is:

1. A portable nasal aspiration system for removing secretion from a user's nasal canals, comprising:
   a sealed, detachable vacuum canister having an attachment device;
   two aspiration tubes for inserting into a users nasal canal, each with one inlet and one outlet;
   a cap forming two apertures spaced apart and supporting the two aspiration tubes, each inlet of the aspiration tubes aligned with a different one of the two apertures such that fluid passes through each aperture independently, a distance between the two aspiration tubes being adjustable to align the aspiration tubes with a user's nasal canals;
   a port, comprising:
      a valve within the port for controlling flow of fluid from the two aspiration tubes, through the port and to the detachable vacuum canister,
      a first attachment end for attaching the port to the cap such that the two apertures are in fluid communication with the valve; and
      a second attachment end for attaching the port to the vacuum canister attachment device such that the valve, when operated, is in fluid communication with a vacuum within the vacuum canister,
   wherein the vacuum canister is sealed and retains a vacuum prior to attaching the vacuum canister attachment device to the second attachment end of the port.

2. The system of claim 1, further comprising an adjustable slider for adjusting the distance between the two aspiration tubes.

3. The system of claim 1, the valve comprising:
   a conduit having a rigid pointed end;
   an attachment mechanism served to block at least one outlet formed on the conduit and to connect the port to the attachment device of the vacuum canister; and
   at least one spring compressed to move the conduit through the attachment mechanism to unblock the at least one outlet, thereby placing the at least one outlet in an operational position.

4. The system of claim 1, wherein the attachment device of the detachable vacuum canister having an aperture thereon, and further comprising a protective film being disposed with the aperture to retain the vacuum within the vacuum canister and penetrable to activate the canister.

5. The nasal aspiration system of claim 1, further comprising attachment straps for fastening the nasal aspiration system to a user.

6. The nasal aspiration system of claim 1, further comprising at least two disposable nasal occluders to cover the aspiration tubes.

7. The nasal aspiration system of claim 1, further comprises attachment mechanisms that connect the first and second attachment ends of the port with the cap and the vacuum canister to form the nasal aspiration system.

8. The nasal aspiration system of claim 7, wherein the attachment mechanisms are selected from a group consisting of one or more notches, snaps, clasps, protrusions, pipes, indentations, apertures, recesses, taps, clips, adhesives, and combination thereof.

* * * * *